United States Patent [19]
Andersson-Schager et al.

[11] Patent Number: 5,466,607
[45] Date of Patent: Nov. 14, 1995

[54] SYSTEM AND METHOD FOR TREATMENT OF A BIOLOGICAL LIQUID

[75] Inventors: Per Andersson-Schager, Kaglinge; Ingemar Johansson; Willy Larsson, both of Sodra Sandby; Erik Lindmark, Lund, all of Sweden

[73] Assignee: Excorim AB, Lund, Sweden

[21] Appl. No.: 146,058

[22] Filed: Apr. 13, 1994

[30] Foreign Application Priority Data

May 10, 1991 [SE] Sweden .................................. 9101413

[51] Int. Cl.⁶ .................................................. A61M 1/03
[52] U.S. Cl. ................... 436/50; 436/52; 436/55; 436/177; 436/179; 436/180; 422/67; 422/81; 604/4; 604/5; 604/6
[58] Field of Search ................... 436/55, 50, 52, 436/180, 177, 179; 422/67, 63, 81, 101; 604/4–6

[56] References Cited

U.S. PATENT DOCUMENTS

| | | | |
|---|---|---|---|
| 3,689,145 | 1/1970 | Judson et al. | 128/214 |
| 4,104,026 | 8/1978 | Brooker et al. | 23/230 B |
| 4,151,844 | 5/1979 | Cullis et al. | 128/214 R |
| 4,708,714 | 11/1987 | Larsson et al. | 604/5 |
| 4,968,295 | 11/1990 | Neumann | 604/6 |

FOREIGN PATENT DOCUMENTS

| | | |
|---|---|---|
| 261530 | 3/1988 | European Pat. Off. . |
| 359319 | 3/1990 | European Pat. Off. . |
| 313933 | 11/1987 | Sweden . |

OTHER PUBLICATIONS

Therapeutic Protein A Immunoadsorption. A review, Transfus. Sci. (1990) vol. 11, pp. 281–302.
Excorim Immunoadsorption System, Brochure, Sweden, (1993).

Primary Examiner—James C. Housel
Assistant Examiner—Long V. Le
Attorney, Agent, or Firm—Lerner, David, Littenberg, Krumholz & Mentlik

[57] ABSTRACT

A method and an apparatus for treatment of a first liquid which is a plasma of human blood comprising cyclically feeding the first liquid and a second liquid to the treatment device, and measuring a component of the first and second liquids so that a ratio between the first and second liquids are determined by a measuring arrangement. The first and second liquids are transferred to predetermined collection points by initiating and terminating a collection of the first liquid during one of the feeding cycles based on the ratio between the first and second liquids. The volume of at least the first liquid conveyed to the treatment device is measured during one of the cycles by a volume measuring arrangement. A theoretical time is determined between the initiating and terminating of the collection of the first liquid.

29 Claims, 2 Drawing Sheets

SYSTEM AND METHOD FOR TREATMENT OF A BIOLOGICAL LIQUID

TECHNICAL FIELD

The present invention relates to a system for treatment of a first liquid in a treatment arrangement which is arranged to be filled alternately by said liquid and a second liquid, whereby the two liquids are periodically mixed with each other and means are arranged for measuring the content of respective liquids in order to convey, depending on the measured value, the principal component of the first liquid to a collection point therefor and the principal component of the second liquid to a second collection point, whereby the collection of the first liquid is initiated at a first mixing ratio and terminated at a second mixing ratio. These two mixing ratios are hereby preferably identical, though they can also be different.

The system according to the invention is primarily intended for treatment of a biological liquid, preferably blood plasma or whole blood.

Many sicknesses are a result of the body's immune system becoming unbalanced, whereby undesirable fractions are formed in the blood. For example, in haemophilia antibodies against factor VIII or factor IX can be formed, which normally control the blood's coagulation.

An object of the present invention is to remove such undesired fractions. Another object is to segregate the removed fractions for further use. For example, the antibodies against said factor VIII or factor IX can themselves be attached to a column for removal of the actual factor VIII or factor IX from other liquids such as blood or plasma from blood donors.

Should it be desired to remove said actual antibodies against factor VIII or factor IX, according to the invention a column is used with factor VIII or factor IX attached to a carrier. Alternatively, protein A or protein G, for example, can be attached to the carrier and have an ability to themselves attach to, amongst others, various different types of IgG. It should also be clear for the skilled man that the invention may also be used in connection with many other adsorption substances.

BACKGROUND ART

The invention can be said to be a direct further development of the art which is described in U.S. Pat. No. 4,708,714. The content of this patent is therefore included in the present description.

The known art is primarily intended for treatment of blood plasma which is alternately mixed with another liquid and whereby the mixture ratio is measured optically. Certain difficulties have manifested themselves through operation in the measuring instrument and also through variations in optical absorbency in the plasma during patient treatment. Variations can be caused by, for example, the patient eating. Employed measuring instruments have therefore often had to be recalibrated. Because of the measuring errors an unnecessarily large quantity of plasma has sometimes been discarded instead of being returned to the patient.

The present invention has therefore as its object to minimize the plasma loss in the system according to the American patent and simultaneously provide a safe, preferably automatic, calibration of measuring instruments used therefore.

DESCRIPTION OF THE INVENTION

The above-mentioned problems are solved according to the invention with help of a system of the above mentioned type which is characterized by means for measuring the quantity of the liquid conveyed to the treatment arrangement during one cycle and by means for theoretically calculating with help of said measured value the time instance at which the collection of the first liquid is to be terminated. If the invention is hereby applied to the technique described in the American patent, it becomes possible to return substantially the same volume to the patient as was taken from the patient and this with minimal plasma loss.

The system according to the invention is preferably provided with means for comparing the measured value for the mixing ratio between the two liquids at said theoretically calculated time instance with a desired value for the time instance when collection of the first liquid is to cease. In this way, it is possible to prolong the collection of the first liquid if the measured value shows that the mixture still contains a high content of the first liquid.

The system according to the invention can alternatively be provided with means for comparing the measured value for the mixing ratio between the two liquids at said theoretically calculated time instance with the measured value of the mixture ratio at the time instance when collection of the first liquid was started. These two values will often be identical, though they can also be in a certain proportion to each other. Preferably, means are hereby arranged to allow the measured values for the mixing ratio at the start and end respectively of the collection of the first liquid during a work cycle to control the value for the mixing ratio at the start of the next work cycle. Should it be desired, for example, to start and cease collection of the first liquid at identical mixture ratios, for example 50%, then the mean value of the two measured values during one work cycle can be allowed to dictate when the collection during the next work cycle will commence.

The system according to the invention is preferably provided with means for measuring said mixing ratio at a time instance or during a time period when only the first liquid is at the measuring site, for use of this measured value in calibrating the measuring arrangement. The measured value should hereby show 100% for the first liquid. If this is not the case, then calibration should be carried out. In practice, however, calibration of the system according to the invention occurs first if the measured value deviates more than a certain percentage, for example more than 2% or 5%. The calibration can be carried out either automatically or manually.

A further improved calibration is achieved if the system according to the invention is provided with means for measuring the mixing ratio at a time instance, or during a time period, when only the second liquid is at the measuring site, for use of this measured value for calibration of the measuring device. The measured value for the mixing ratio should hereby show 0% for the first liquid. If this is not the case, then calibration should be carried out. Even in this case, in practice a calibration according to the invention occurs only if the measured value deviates more than a certain percentage, for example 2% or 5%.

Preferably the calibration is arranged to take place first before the subsequent cycle for simplification of the comparison between values measured during one cycle. Alternatively, however, the calibration can be arranged to take place substantially immediately for quick attainment of the correct measured values.

As mentioned above, the system according to the invention is primarily intended to be used for treatment of a biological liquid, preferably blood plasma, whereby said treatment arrangement comprises an adsorption column for removal of non-desirable substances, such as anti-bodies, from the biological liquid. Preferably two columns are hereby used in parallel for alternate adsorption and elution of adsorbed substances, as described in said above mentioned American patent.

BEST MODE OF CARRYING OUT THE INVENTION

Figure 1:
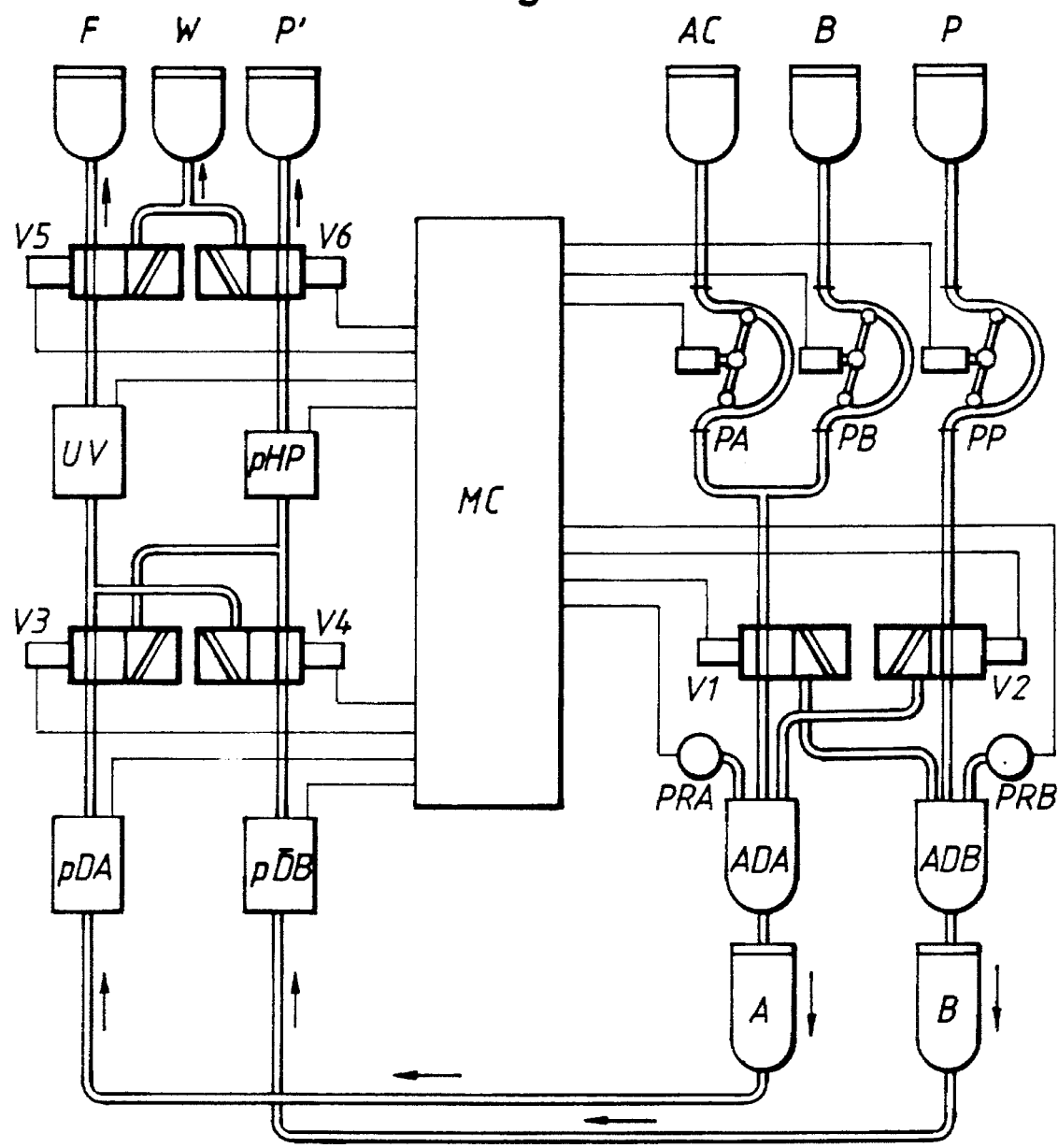
FIG. 1 shows schematically a block diagram of a system according to the invention.

Two columns A and B are shown in FIG. 1 which are intended to alternately adsorb undesired substances from plasma which, with help of a pump PP, is pumped from a source P for such plasma. The source can, for example, be connected via a plasma filter directly to a patient.

The plasma is supplied via a valve V2 either to a drop chamber ADA connected before the column A or to a drop chamber ADB connected before the column B. Both the drop chambers are provided with pressure measuring means PRA and PRB respectively, which, together with the pump PP and the valve V2, are connected to a microprocessor MC. A valve V1 and two pumps PA and PB are also connected to this microprocessor. With help of the valve V1 and the pump PB a buffer can be pumped from a source B of such a liquid to the column which is temporarily not being used for adsorption. In this way, plasma is displaced in said column which is controlled with help of preferably optical measuring means PDA and PDB. When the plasma is totally displaced, a second pump PA is instead connected which pumps an elution liquid, for example an acid, from a source AC for said liquid. The hereby eluted fraction is also controlled with help of the measuring means PDA and PDB, which are also connected to the microprocessor MC. The same applies for the subsequent valves V3 and V4. With help of these valves, the pumped liquid can thereafter be pumped to either a more accurate protein content measurer, for example a UV-measurer, or to a pH-measurer pHP. Both these measurers UV and pHP respectively are connected to the microprocessor MC. The pumped liquid thereafter reaches two valves V5 and V6, which are also connected to the microprocessor MC. Depending on the measured values from the two latter-mentioned measuring means, respective liquids are then conveyed either to a collection point F for the eluted fraction or to a collection point P' for the plasma or to a drain or to other collection point W. The collection point P' can, of course, be a patient who is under treatment with help of the system according to the invention.

Figure 2:
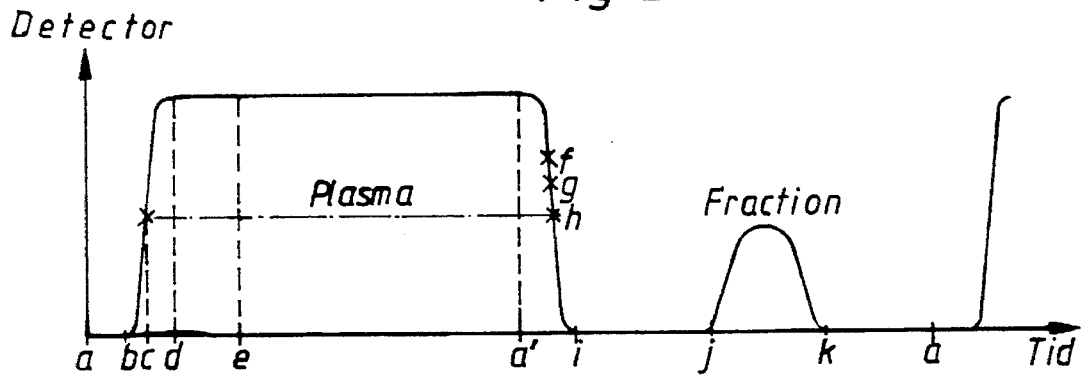
FIG. 2 shows a time diagram for a work cycle in the system according to FIG. 1.

In FIG. 2 there is shown a time cycle for plasma treatment, which is possible to implement with help of the system shown in FIG. 1. If we imagine that the time cycle concerns the column A, then the point a denotes the instance when the valve V2 begins to permit plasma to flow in the direction towards column A. The point b denotes the instance when the plasma reaches the measuring device PDA. The point c denotes the instance when the valve V3 begins to allow the flow of the plasma mixture towards the measurer pHP for further conveyance to the valve V6 and the collection point P' for plasma. Should an unsuitable pH value be measured, the plasma mixture is instead conveyed via valve V6 to the collection point W, for example a sink. At the point d the measurer PDA shows a measured value which corresponds to 100% plasma. This measured value is suitably integrated in the microprocessor MC during a certain time period, for example up to the point e. The hereby integrated value is then used for calibration of the measuring means PDA. This calibration can either occur directly or first just before commencement of the next cycle. During the collection time for the plasma P, the volume of the liquid pumped to the column A is measured. This can be achieved, for example, by counting the number of pump revolutions of the pump PP. Just before the end of the collection period, however, the valves V1 and V2 change over and from this time instance the number of pump revolutions for the pump PB is instead calculated. The pumped quantity is stored in the microprocessor MC which, at the same time, calculates a theoretical time instance at which the collection of plasma is to be interrupted. At this time instance, which in FIG. 2 is denoted by f, the plasma collection can be interrupted. Preferably, however, the hereby measured value for the mixture ratio is compared with a desired value and if the first mentioned value is too high, the collection period can be prolonged, for example up to the point g. The hereby measured value of the mixture ratio is suitably used for control of the starting of the collection during the next work cycle.

The point h denotes the desired mixing ratio at the interruption of the plasma collection. This value is suitably the same for the points c and h, for example 50% plasma.

At the point i the measuring means PDA shows a measured value which corresponds to 0% plasma. At, or just after, this point the pump PB is stopped and the pump PA is instead activated which pumps elution liquid via the valve V1 and the drop chamber ADA to the column A. At the point j the measuring means PDA shows that the eluted fraction has reached the measuring means and at the point k the same measuring means shows that fraction no longer reaches it. The eluted fraction is collected via the valve V3, the measurer UV and the valve V5 at the collection point F therefor. The collection can hereby already begin before the point j and be interrupted after the point k. This means only that the fraction will be somewhat more diluted by either elution liquid from the source AC or buffer liquid from the source B. The point a then denotes the commencement of a new work cycle for the column A. The column B's work cycle is identical to that of column A, but commences with the changeover of valves V1 and V2 and, more precisely, at the point a'.

The above described zero-calibration can occur either between the points i and j or between the points k and a.

Figure 3:
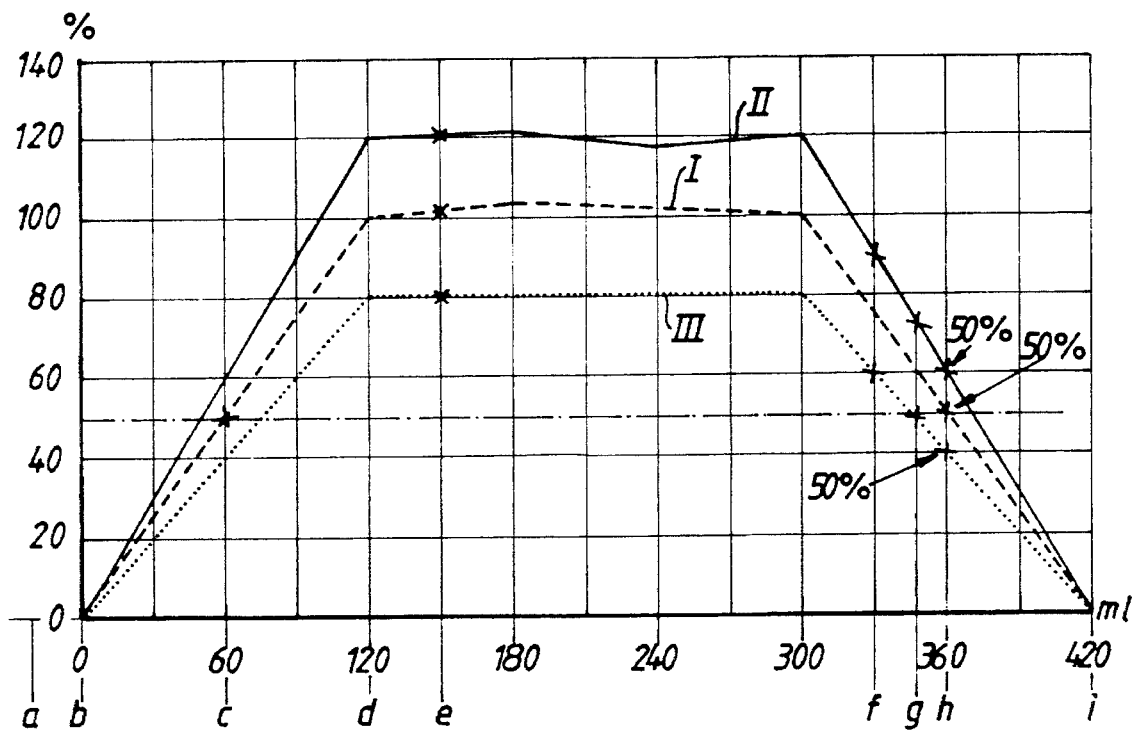
FIG. 3 shows a similar diagram for a part of the work cycle, though here a measured detector value is compared with the pumped volume of liquid.

The points a–i also appear in FIG. 3, which shows the measured value in either of the measuring means PDA or PDB in comparison with the volume pumped during a certain time period to either of the columns A and B. If it should be the column A, then the point a denotes the time instance when valve V2 switches over and begins to direct plasma towards the column A and the point i denotes the time instance when the measurer PDA can no longer detect any plasma in the pumped liquid.

FIG. 3 displays three curves, whereby the curve I denotes an ideal curve with a substantially correctly adjusted measuring device PDA during the whole time, whereby the plasma collection is started at the point c at the mixing ratio 50% and is interrupted at the point h at the same mixing ratio.

According to the curve II, the measurer PDA instead shows a maximum mixing ratio of 120% plasma depending on, for example, operation of the measuring device or the fact that the patient has eaten. This is discovered at the measuring instance e and the measured value is used for calibration of the measurer PDA either directly or just before the next work cycle.

According to the curve III, the measurer PDA in the same way shows a mixing ratio of 80%, when the value should instead be 100%. The measuring device is therefore calibrated in the other way.

FIG. 3 shows that with the correct measured values for the measurer PDA, plasma is collected during the whole time that the mixture contains more than 50% plasma. Should, however, the curve II be followed, plasma is collected already at the mixture ratio 50:120 and is interrupted, if the mixture ratio is allowed so to determine, at the same mixture ratio. This is not so important for the patient, but may give rise to a certain increase in the patient's weight.

Should, however, the curve III be followed, the plasma collection commences first with the mixture ratio 50:80 and is interrupted at the same mixture ratio. This is on the condition that the measured value is also allowed to interrupt the plasma collection. This condition is more dangerous since the patient can hereby lose a considerable quantity of plasma and can receive a lack of, for example, albumin.

According to the invention, however, the measured value of the mixture ratio is not allowed to interrupt the plasma collection on its own. Instead, this is interrupted, as described above, firstly depending on the liquid volume pumped to the adsorption column and secondly on the measured value at a theoretically calculated time instance at which the desired quantity of liquid has been pumped to the adsorption column.

Naturally, the invention is not restricted to solely the above described embodiment, but can be varied within the scope of the appended claims. For example, the time and volume conditions shown in FIGS. 2 and 3 can be varied within wide limits depending on the type of treatment.

We claim:

1. A method for the treatment of a first liquid which is a plasma of human blood in a treatment device comprising the steps of:

cyclically feeding said first liquid and a second liquid to said treatment device, measuring a component of said first and second liquids whereby a ratio between said first and second liquids being determined by a measuring arrangement, transferring said first and second liquids to predetermined collection points by initiating and terminating a collection of said first liquid during one of said feeding cycles based on said ratio between said first and second liquids, measuring the volume of at least said first liquid conveyed to said treatment device during said one of said cycles by a volume measuring arrangement, and determining a theoretical time between said initiating and said terminating of said collection of said first liquid based thereon.

2. The method of claim 1 wherein said treatment device includes a pair of treatment devices, said method including cyclically feeding said first and second liquids alternately to said pair of treatment devices.

3. The method of claim 1 including comparing said measured value of said ratio between said first and second liquids at said predetermined theoretical time to a desired value for said time between said initiating and said terminating of said collection of said first liquid.

4. The method of claim 3 including extending said theoretical time between said initiating and said terminating of said collection of said first liquid to said desired value for said time between said initiating and said terminating of said collection of said first liquid when said desired value is greater than said theoretical time.

5. The method of claim 1 including determining said ratio of said first and second liquids at a time when said component of said second liquid is not present in a mixture of said first and second liquids whereby said measuring of said components may be calibrated therefrom.

6. The method of claim 1 including determining said ratio of said first and second liquids at a time when said component of said first liquid is not present in a mixture of said first and second liquids whereby said measuring of said components may be calibrated therefrom.

7. The method of claim 5 or 6 including calibrating said measure of said components prior to cycles subsequent to said one of said cycles in order to simplify comparison between measurements conducted during said subsequent cycle.

8. The method of claim 5 or 6 including calibrating said measuring of said component in order to obtain the correct measured value.

9. The method of claim 1 including comparing the measured value for said ratio between said first and second liquids at said determined theoretical time to the measured value of said ratio between said first and second liquids at said initiation of said collection of said first liquid.

10. The method of claim 1 wherein said first liquid comprises a biological liquid.

11. The method of claim 10 wherein said biological liquid comprises blood plasma.

12. The method of claim 11 wherein said treatment device comprises an adsorption column.

13. The method of claim 2 wherein said first liquid comprises a biological liquid and said pair of treatment devices comprise adsorption columns.

14. A system for treating a separated fraction of a biological fluid, comprising:

a first fluid which is a separated fraction of a biological fluid;

an adsorption column having an adsorption medium therein for removal of undesirable substances from said first fluid;

primary valve means situated upstream of said adsorption column for alternately directing said first fluid and a second fluid to said adsorption column;

secondary valve means situated downstream of said adsorption column for selectively directing said first fluid to a first collection point by initiating and terminating collection of said first fluid at said first collection point;

ratio measuring means situated between said adsorption column and said secondary valve means for measuring a ratio of a mixture of said first and second fluids;

volume measuring means for measuring a volume of said first and second fluids passing said adsorption column; and determination means for controlling said secondary valve means including means for calculating a theoretical time instance when said secondary valve means terminates said collection of the first fluid depending upon signals from said ratio measuring means and said volume measuring means.

15. The system of claim 14, wherein said first fluid is a plasma of human blood and said undesirable substance is human IgG.

16. The system of claim 15, wherein said primary valve means comprises a plurality of valve members for alternately directing said first fluid to said adsorption column and to a second column.

17. The system of claim 15, wherein said determination means further comprises comparing means for comparing ratio between a measured value of said ratio at said theoretical time instance with a threshold value for prolonging the collection of the first fluid while said measured value indicates if said mixture of said first and second fluids contain a high content of the first fluid.

18. The system of claim 15, further comprising calibration means for calibrating said ratio measuring means during at least a first segment of time when substantially only said first fluid is present in said ratio measuring means and a second segment of time when substantially only said second fluid is present in said ratio measuring means.

19. The system of claim 15, wherein said volume measuring means determines a first volume from said initiation of the primary value means to initiation of the collection of said first fluid, and a second volume from said initiation of the primary valve means to direct the second fluid to said adsorption column and the termination of the collection of said first fluid; and said determination means controlling said secondary valve means depending upon said measured ratio being above a desired ratio, said desired ratio being adjusted so that said first and second volumes are substantially equal.

20. The system of claim 11, wherein said determination means comprises adjustment means for adjusting said desired value to be the value of the ratio at the termination and the ratio at the collection of said first fluid in a previous collection phase.

21. The system of claim 11, further comprising calibration means for calibrating said ratio measuring means during at least said first segment of time when substantially only said first fluid is present in said ratio measuring means and said second segment of time when substantially only the second fluid is present in said ratio measuring means.

22. A method for the treatment of a first liquid which is a separated fraction of a biological fluid, comprising the steps of:

removing undesirable substances from said first fluid in an adsorption column having an adsorption medium therein;

alternately directing said first fluid and a second fluid to said adsorption column by a primary valve arrangement situated upstream of said adsorption column;

selectively directing said first fluid to a first collection point by initiating and terminating collection of said first fluid at said first collection point by a secondary valve arrangement situated downstream of said adsorption column;

measuring a ratio of a mixture of said first and second fluids by a measuring arrangement situated between said adsorption column and said secondary valve arrangement;

measuring a volume of said first and second fluids passing said adsorption column by a volume measuring arrangement; and controlling said secondary valve arrangement by a determining of a theoretical time instance when said secondary valve arrangement terminates said collection of said first fluid depending upon signals from said ratio measuring arrangement and said volume measuring arrangement.

23. The method of claim 22, wherein said first fluid is a plasma of human blood and said undesirable substance is human IgG.

24. The method of claim 22, wherein said primary valve arrangement comprises a purality of valve members for alternately directing said first fluid to said adsorption column and to a second column.

25. The method of claim 22, wherein said determination arrangement further comprises a comparing device for comparing ratio between a measured value of said ratio at said theoretical time instance with a threshold value for prolonging the collection of said first fluid while the measured value indicates if said mixture of said first and second fluids still contain a high content of said first fluid.

26. The method of claim 22, further comprising the step of calibrating said ratio measuring device during at least a first segment of time when substantially only said first fluid is present in said ratio measuring arrangement and a second segment of time when substantially only said second fluid is present in said ratio measuring arrangement.

27. The method of claim 22, wherein said volume measuring arrangement determines a first volume from said initiation of the primary valve arrangement to initiation of said collection of said first fluid, and a second volume from said initiation of said primary valve arrangement to direct the second fluid to said adsorption column and the termination of collection of said first fluid; and said determination arrangement controlling said secondary valve means depending upon said measured ratio being above a desired ratio, said desired ratio being adjusted so that the first and second volumes being substantially equal.

28. The method of claim 27, wherein said determination arrangement comprises an adjustment device for adjusting said desired value to be the value of the ratio at the termination and the ratio at the collection of said first fluid in a previous collection phase.

29. The method of claim 27, further comprising the step of calibrating said ratio measuring arrangement during at east said first segment of time when substantially only said first fluid is present in said ratio measuring arrangement and said second segment of time when substantially only the second fluid is present in said ratio measuring arrangement.

* * * * *

UNITED STATES PATENT AND TRADEMARK OFFICE
CERTIFICATE OF CORRECTION

PATENT NO. : 5,466,607
DATED : November 14, 1995
INVENTOR(S) : Per Andersson-Schager; Ingemar Johansson; Willy Larsson; Erik Lindmark It is certified that error appears in the above-identified patent and that said Letters Patent is hereby corrected as shown below:

Title page, item [22] should read --PCT Filed: April 3, 1992--

After item [22] insert:

--[86] PCT No.: PCT/SE92/00217
§ 371 Date: Apr. 13, 1994
§ 102(e) Date: Apr. 13, 1994
[87] PCT No.: WO92/20384
PCT Pub. Date: Nov. 26, 1992--

Column 7, line 34, delete "11" and insert therefor --19--.
Column 7, line 39, delete "11" and insert therefor --19--.
Column 8, line 53, delete "east" and insert therefor --least--.

Signed and Sealed this

Nineteenth Day of March, 1996

Attest:

BRUCE LEHMAN

Attesting Officer      Commissioner of Patents and Trademarks